(12) United States Patent
Brannan

(10) Patent No.: US 8,328,800 B2
(45) Date of Patent: *Dec. 11, 2012

(54) DIRECTIVE WINDOW ABLATION ANTENNA WITH DIELECTRIC LOADING

(75) Inventor: Joseph D. Brannan, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 590 days.

This patent is subject to a terminal disclaimer.

(21) Appl. No.: 12/535,856

(22) Filed: Aug. 5, 2009

(65) Prior Publication Data
US 2011/0034913 A1 Feb. 10, 2011

(51) Int. Cl.
*A61B 18/18* (2006.01)
(52) U.S. Cl. .......... 606/41; 607/154; 607/156
(58) Field of Classification Search ............ 606/32, 606/33, 34, 41; 607/101, 154, 156
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,776,086 A * | 10/1988 | Kasevich et al. | 29/828 |
| 4,798,215 A | 1/1989 | Turner | |
| 4,823,812 A * | 4/1989 | Eshel et al. | 607/156 |
| 5,097,844 A | 3/1992 | Turner | |
| 5,301,687 A | 4/1994 | Wong et al. | |
| 5,417,210 A | 5/1995 | Funda et al. | |
| 5,599,295 A | 2/1997 | Rosen et al. | |
| 5,720,718 A | 2/1998 | Rosen et al. | |
| 6,031,375 A | 2/2000 | Atalar et al. | |
| 6,245,062 B1 * | 6/2001 | Berube et al. | 606/33 |
| 6,289,249 B1 | 9/2001 | Arndt et al. | |
| 6,325,796 B1 | 12/2001 | Berube et al. | |
| 6,375,606 B1 | 4/2002 | Garibaldi et al. | |
| 6,398,781 B1 | 6/2002 | Goble et al. | |
| 6,451,015 B1 | 9/2002 | Rittman, III et al. | |
| 6,582,427 B1 | 6/2003 | Goble et al. | |
| 6,603,994 B2 | 8/2003 | Wallace et al. | |
| 6,723,091 B2 | 4/2004 | Goble et al. | |
| 6,725,080 B2 | 4/2004 | Melkent et al. | |
| 7,301,131 B2 * | 11/2007 | Gauthier et al. | 219/679 |

(Continued)

FOREIGN PATENT DOCUMENTS

DE 390937 3/1924

(Continued)

OTHER PUBLICATIONS

International Search Report EP10008140 dated Jan. 12, 2011.

(Continued)

*Primary Examiner* — Michael Peffley
*Assistant Examiner* — Jocelyn D Ram

(57) ABSTRACT

An electrosurgical device for directing energy to a target volume of tissue includes a coaxial feedline having an inner conductor, an outer conductor coaxially disposed around the inner conductor, and a dielectric material disposed therebetween. An elongated electrically-conductive member is longitudinally disposed at a distal end of the inner conductor. A balun structure is disposed on the outer conductor. The device also includes an electrically-conductive cylinder coaxially disposed around a distal portion of the balun structure, and a dielectric structure disposed substantially adjacent to a distal end of the electrically-conductive cylinder, wherein the dielectric structure longitudinally extends from the distal end of the electrically-conductive cylinder to a distal end of the electrically-conductive member.

15 Claims, 11 Drawing Sheets

U.S. PATENT DOCUMENTS

| | | |
|---|---|---|
| 7,311,703 B2 * | 12/2007 | Turovskiy et al. ............... 606/33 |
| 7,439,736 B2 | 10/2008 | Meaney et al. |
| 7,467,015 B2 | 12/2008 | Van der Weide |
| 7,565,207 B2 | 7/2009 | Turner et al. |
| 7,875,024 B2 | 1/2011 | Turovskiy et al. |
| 8,035,570 B2 | 10/2011 | Prakash et al. |
| 8,059,059 B2 | 11/2011 | Bonn |
| 8,118,808 B2 | 2/2012 | Smith et al. |
| 2002/0022836 A1 | 2/2002 | Goble et al. |
| 2003/0083654 A1 * | 5/2003 | Chin et al. ...................... 606/41 |
| 2003/0153908 A1 | 8/2003 | Goble et al. |
| 2004/0097805 A1 | 5/2004 | Verard et al. |
| 2004/0242992 A1 | 12/2004 | Hareyama |
| 2006/0155270 A1 | 7/2006 | Hancock |
| 2007/0106332 A1 * | 5/2007 | Denker et al. .................... 607/2 |
| 2007/0233057 A1 | 10/2007 | Konishi |
| 2010/0305559 A1 * | 12/2010 | Brannan et al. ................. 606/33 |
| 2011/0034917 A1 * | 2/2011 | Brannan ........................ 606/41 |
| 2011/0040300 A1 * | 2/2011 | Brannan ........................ 606/41 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 371151 | 6/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 034 748 | 9/2000 |
| EP | 1 159 926 | 5/2001 |
| EP | 1 278 007 | 1/2003 |
| EP | 1 810 627 | 7/2007 |
| EP | 2255742 | 12/2010 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | 00/53112 | 9/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |

OTHER PUBLICATIONS

U.S. Appl. No. 10/244,346, filed Sep. 16, 2002, Abandoned.
U.S. Appl. No. 12/023,606, filed Jan. 31, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009, Patent 7642451.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.

U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anohymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Heniostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.

Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662; Sep. 1983.
Joseph Ortenberg, " LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210, abstract only.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184, abstract only.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol. vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, Vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar vessel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
S. Humphries Jr. et al., "FiniteElement Codes to Model Electrical Heating and Non•LInear Thermal Transport in Biological Media", Proc. ASME HTD-355, 131 (1997).
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.

European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8. 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, filed Jun. 7, 1995.
U.S. Appl. No. 08/136,098, filed Oct. 14, 1993.
European Search Report EP 06020584.6 dated Feb. 1, 2007.

* cited by examiner

DIRECTIVE WINDOW ABLATION ANTENNA WITH DIELECTRIC LOADING

BACKGROUND

1. Technical Field

The present disclosure relates to electrosurgical devices suitable for use in tissue ablation applications and, more particularly, to electrosurgical devices with directional radiation patterns.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis.

A microwave transmission line typically includes a thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, e.g., a length of transmission line or coaxial cable, is provided with a plurality of openings through which energy "leaks" or radiates away from the guiding structure. This type of construction is typically referred to as a "leaky coaxial" or "leaky wave" antenna.

Some ablation targeted lesions are too small or too hard to be punctured by an ablation probe. In these cases, doctors may place the probe as close as possible to the lesion and perform an ablation. With non-directional ablation probes, the ablation may radiate to both sides of the probe which may damage healthy tissue located on the non-tumor side of the radiating section.

During certain procedures, it can be difficult to assess the extent to which the microwave energy will radiate into the surrounding tissue, making it difficult to determine the area or volume of surrounding tissue that will be ablated.

SUMMARY

The present disclosure relates to a device for directing energy to a target volume of tissue including a coaxial feedline having an inner conductor, an outer conductor coaxially disposed around the inner conductor, and a dielectric material disposed therebetween. An elongated electrically-conductive member is longitudinally disposed at a distal end of the inner conductor. A balun structure is disposed on the outer conductor. The device includes an electrically-conductive cylinder coaxially disposed around a distal portion of the balun structure. The device also includes a dielectric structure disposed substantially adjacent to a distal end of the electrically-conductive cylinder, wherein the dielectric structure longitudinally extends from the distal end of the electrically-conductive cylinder to a distal end of the electrically-conductive member.

The present disclosure also relates to a method for manufacturing an electrosurgical device including the step of providing a coaxial feedline having an inner conductor, an outer conductor, and a dielectric material disposed therebetween, and joining an electrically-conductive member to a distal end of the inner conductor at a distal end of the coaxial feedline. The method also includes the steps of: forming a dielectric layer around a distal portion of the outer conductor; forming an electrically-conductive layer around a proximal portion of the dielectric layer such that the electrically-conductive layer is electrically coupled to the outer conductor; joining an electrically-conductive cylinder to distal portion of the electrically-conductive layer; and forming a dielectric structure disposed substantially adjacent to a distal end of the electrically-conductive cylinder, wherein the dielectric structure longitudinally extends from the distal end of the electrically-conductive cylinder to a distal end of the electrically-conductive member.

BRIEF DESCRIPTION OF THE DRAWINGS

Objects and features of the presently disclosed antenna assemblies will become apparent to those of ordinary skill in the art when descriptions of various embodiments thereof are read with reference to the accompanying drawings, of which.

DETAILED DESCRIPTION

Figure 1:
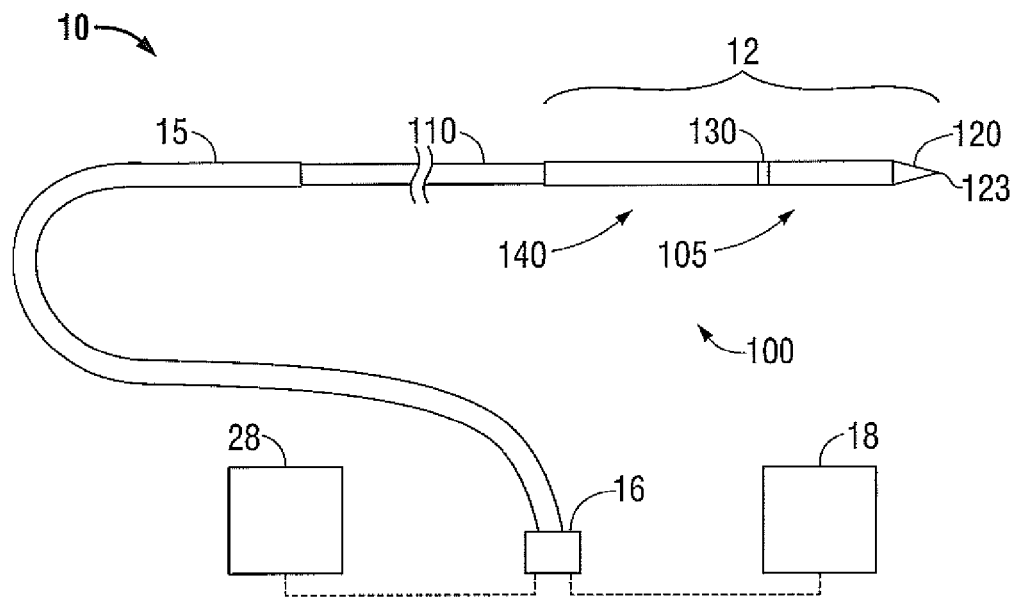
FIG. 1 is a schematic diagram of an ablation system according to an embodiment of the present disclosure.

Hereinafter, embodiments of the presently disclosed electrosurgical device with a directional radiation pattern will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is further from the user.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation assisted resection. As it is used in this description, "transmission line" generally refers to any transmission medium that can be used for the propagation of signals from one point to another.

Various embodiments of the present disclosure provide electrosurgical devices for treating tissue and methods of directing electromagnetic radiation to a target volume of tissue. Embodiments may be implemented using electromagnetic radiation at microwave frequencies or at other frequencies. An electrosurgical system including an energy applicator, according to various embodiments, is designed and configured to operate between about 500 MHz and about 10 GHz with a directional radiation pattern.

Various embodiments of the presently disclosed electrosurgical device with a directional radiation pattern are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

FIG. 1 shows an electrosurgical system 10 according to an embodiment of the present disclosure that includes an energy applicator or probe 100. Probe 100 generally includes an antenna assembly 12 having a radiating portion connected by a feedline 110 (or shaft) via a transmission line 15 to a connector 16, which may further operably connect the probe 100 to an electrosurgical power generating source 28, e.g., a microwave or RF electrosurgical generator.

Feedline 110 may be formed from a suitable flexible, semi-rigid or rigid microwave conductive cable and may connect directly to an electrosurgical power generating source 28. Alternatively, the feedline 110 may electrically connect the antenna assembly 12 via the transmission line 15 to the electrosurgical power generating source 28. Feedline 110 may have a variable length from a proximal end of the antenna assembly 12 to a distal end of transmission line 15 ranging from a length of about one inch to about twelve inches. Feedline 110 may be formed of suitable electrically conductive materials, e.g., copper, gold, silver or other conductive metals having similar conductivity values. Feedline 110 may be made of stainless steel, which generally offers the strength required to puncture tissue and/or skin. Conductive materials used to form the feedline 110 may be plated with other materials, e.g., other conductive materials, such as gold or silver, to improve their properties, e.g., to improve conductivity, decrease energy loss, etc. In some embodiments, the feedline 110 includes stainless steel, and to improve the conductivity thereof the stainless steel may be coated with a layer of a conductive material such as copper or gold. Feedline 110 may include an inner conductor, a dielectric material coaxially surrounding the inner conductor, and an outer conductor coaxially surrounding the dielectric material. Antenna assembly 12 may be formed from a portion of the inner conductor that extends distal of the feedline 110 into the antenna assembly 12. Feedline 110 may be cooled by fluid e.g., saline or water, to improve power handling, and may include a stainless steel catheter.

In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. Transmission line 15 may additionally, or alternatively, provide a conduit (not shown) configured to provide coolant from a coolant source 18 to the probe 100.

Located at the distal end of the antenna assembly 12 is an end cap or tapered portion 120, which may terminate in a sharp tip 123 to allow for insertion into tissue with minimal resistance. The end cap or tapered portion 120 may include other shapes, such as, for example, a tip 123 that is rounded, flat, square, hexagonal, or cylindroconical.

In some variations, the antenna assembly 12 includes a distal radiating portion 105 and a proximal radiating portion 140. A junction member 130 may be provided. Junction member 130, or portions thereof, may be disposed between the proximal and distal radiating portions, 140 and 105, respectively. In some embodiments, the distal and proximal radiating portions 105, 140 align at the junction member 130, which is generally made of a dielectric material, e.g., adhesives, and are also supported by the inner conductor that extends at least partially through the distal radiating portion 105. Junction member 130 may be formed from any suitable elastomeric or ceramic dielectric material by any suitable process. In some embodiments, the junction member 130 is formed by overmolding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E.I. du Pont de Nemours and Company of Wilmington, Del., United States). Junction member 130 may be formed using any suitable over-molding compound by any suitable process, and may include use of a ceramic substrate.

In some embodiments, the antenna assembly 12 may be provided with a coolant chamber (not shown). Additionally, the junction member 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", now issued U.S. Pat. No. 8,118,808, and U.S. Pat. No. 7,311,703 entitled "DEVICES AND METHODS FOR COOLING MICROWAVE ANTENNAS".

In some embodiments, the antenna assembly 12 may be provided with an outer jacket (not shown) disposed about the distal radiating portion 105, the junction 130 and/or the proximal radiating portion 140. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition. The outer jacket may be a water-cooled catheter formed of a material having low electrical conductivity.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may provide ablations in short procedure times, e.g., a few minutes, to destroy cancerous cells in the target tissue region.

A plurality of probes 100 may be placed in variously-arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

In operation, microwave energy having a wavelength, lambda ($\lambda$), is transmitted through the antenna assembly 12, e.g., along the proximal and distal radiating portions 140, 105, and radiated into the surrounding medium, e.g., tissue. The length of the antenna for efficient radiation may be dependent on the effective wavelength $\lambda_{eff}$, which is dependent upon the dielectric properties of the medium being radiated. Antenna assembly 12 through which microwave energy is transmitted at a wavelength $\lambda$ may have differing effective wavelengths $\lambda_{eff}$ depending upon the surrounding medium, e.g., liver tissue, as opposed to breast tissue.

Figure 2:
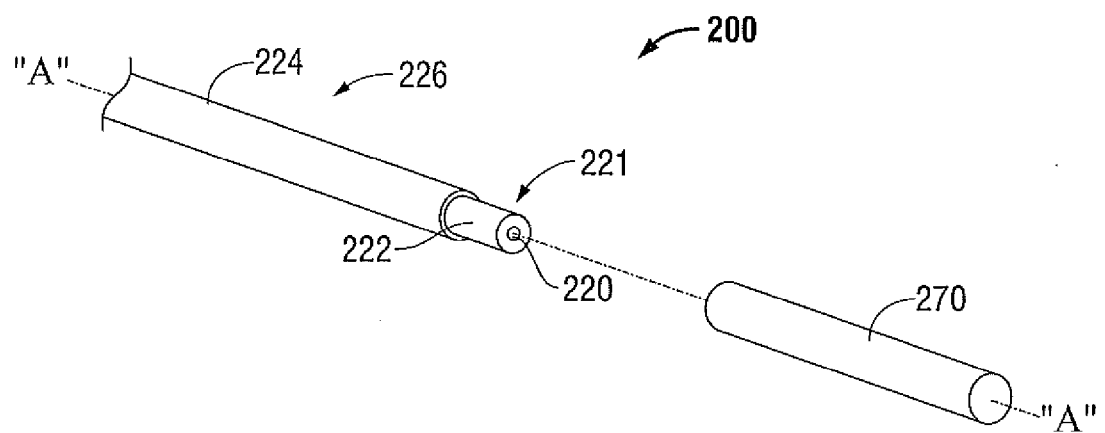
FIG. 2 is a perspective view with parts separated of a portion of an energy applicator according to an embodiment of the present disclosure.

FIGS. 2 through 12 show a sequentially-illustrated, assembly of components forming an energy applicator or probe having a dielectric loaded aperture (e.g., "W" shown in FIG. 14), in accordance with the present disclosure. In FIG. 2, a coaxial feedline 226 is shown with the outer conductor 224 trimmed back, such that a portion 221 of the dielectric material 222 and the inner conductor 220 extends beyond the outer conductor 224. According to an embodiment of the present disclosure, an energy applicator or probe (shown generally as 200 in FIG. 2) includes an electrically conductive element 270 that extends along the longitudinal axis "A" of the energy applicator 200. Electrically conductive element 270 may be positioned in a distal portion of the probe 200. In some embodiments, the electrically-conductive member 270 is a solid metal cylinder disposed at the distal end of the portion 221 electrically coupled to the inner conductor 220 (e.g., by solder). Electrically conductive element 270 may be formed of any suitable electrically-conductive material (e.g., metal such as stainless steel, aluminum, titanium, copper, etc.) of any suitable length. The shape and size of the electrically conductive element 270 may be varied from the configuration depicted in FIG. 2.

Figure 3:
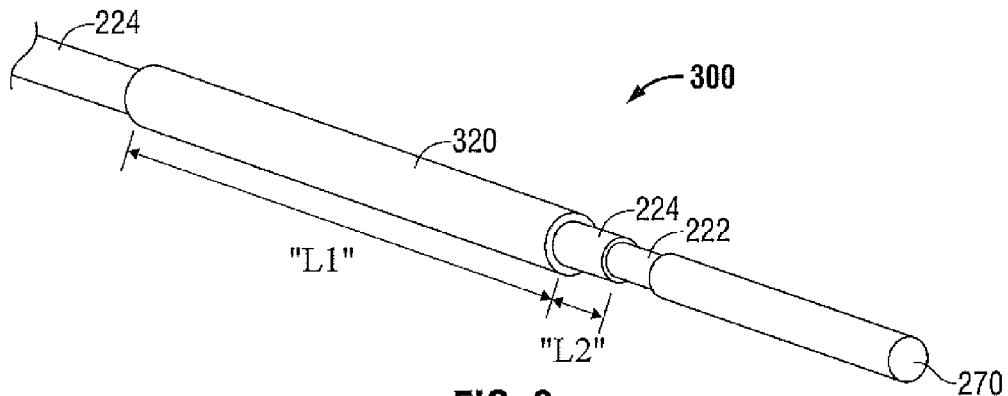
FIG. 3 is a perspective, assembled view of the portion of the energy applicator of FIG. 2 shown with a dielectric layer disposed about a portion of the outer conductor according to an embodiment of the present disclosure.

FIG. 3 shows an energy applicator 300 according to an embodiment of the present disclosure that similar to the energy applicator 200 of FIG. 2, except for a dielectric layer 320 (also referred to herein as a balun insulator) disposed coaxially about a distal portion of the outer conductor 224 of the feedline 226. Dielectric layer 320 may have a suitable length "L1" in a range from about 0.1 inches to about 3.0 inches. The length "L1" may depend on the dielectric constant of dielectric layer 320 and frequency. Dielectric layer 320 may be spaced apart from and disposed proximal to the distal end of the outer conductor 224. In some embodiments, the dielectric layer 320 is spaced apart, by a length "L2", e.g., about 0.1 inches, from the distal end of the outer conductor 224. Balun insulator 320 may extend distally beyond the distal end of the conductive balun sleeve (e.g., 430 shown in FIG. 4) to direct current into a balancing/unbalancing (balun) structure (e.g., "B" shown in FIG. 4). Dielectric layer 320 may be formed of any suitable insulative material, including, but not limited to, ceramics, water, mica, polyethylene, polyethylene terephthalate, polyimide, polytetrafluoroethylene (PTFE) (e.g., Teflon®, manufactured by E.I. du Pont de Nemours and Company of Wilmington, Del., United States), glass, metal oxides or other suitable insulator, and may be formed in any suitable manner. Dielectric layer 320 may be grown, deposited or formed by any other suitable technique. In some embodiments, the balun insulator 320 is formed from a material with a dielectric constant in the range of about 1.7 to about 10. The shape, size and relative position of the balun insulator 320 may be varied from the configuration depicted in FIG. 3.

Figure 4:
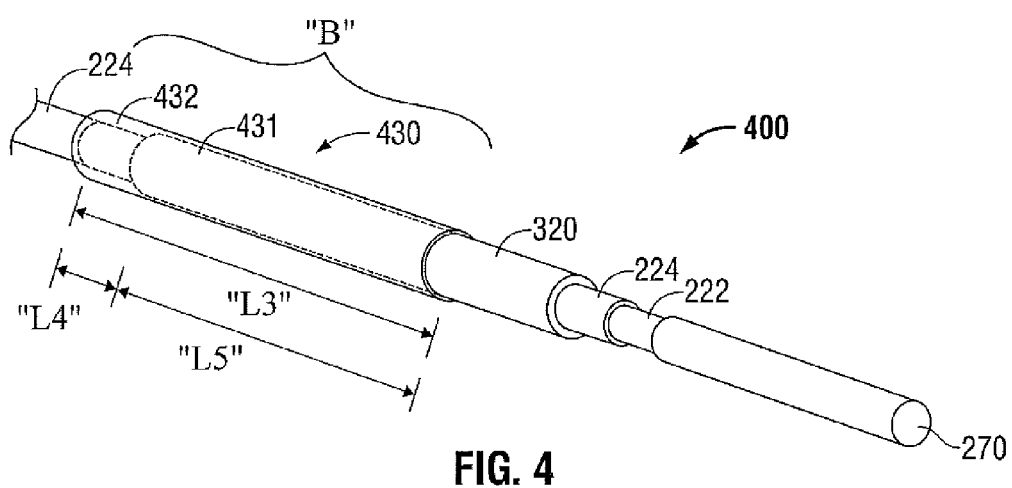
FIG. 4 is a perspective view of the portion of the energy applicator of FIG. 3 shown with an electrically-conductive layer disposed about a portion of the dielectric layer according to an embodiment of the present disclosure.

FIG. 4 shows an energy applicator 400 according to an embodiment of the present disclosure that is similar to the energy applicator 300 of FIG. 3 except for an electrically-conductive layer 430 (also referred to herein as a conductive balun sleeve) disposed coaxially about a proximal portion of the energy applicator 400. Electrically-conductive layer 430 may have any suitable length "L3", e.g., about 0.1 inches to about 3.0 inches. Length "L1" may depend on the dielectric constant of dielectric layer 320 and frequency. Electrically-conductive layer 430 may be formed as a single structure and electrically coupled to the outer conductor 224, e.g., by solder or other suitable electrical connection. In some embodiments, the electrically-conductive layer 430 includes a first portion 431, having a length "L5", disposed coaxially about a proximal portion of the dielectric layer 320, and a second portion 432, having a length "L4", disposed proximally to the first portion 431 electrically coupled to the outer conductor 224. First and second portions 431, 432 may be formed of any suitable electrically-conductive material, e.g., metal such as stainless steel, titanium, copper, etc., and may be formed in any suitable manner. First and second portions 431, 432 may be formed separately from each other. First and second portions 431, 432 may form a single, unitary structure. The shape and size of the electrically-conductive balun sleeve 430 may be varied from the configuration depicted in FIG. 4.

Figure 5:
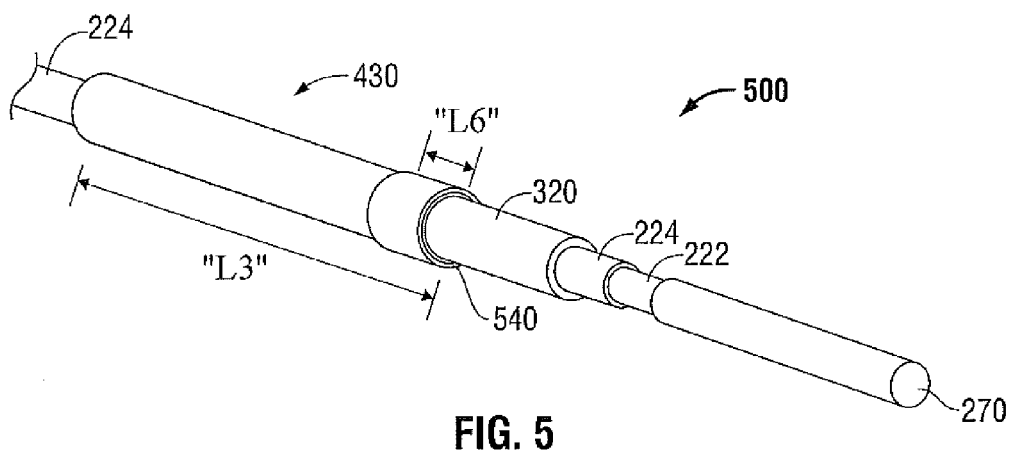
FIG. 5 is a perspective view of the portion of the energy applicator of FIG. 4 shown with an electrically-conductive cylinder disposed about the distal end of the electrically-conductive layer according to an embodiment of the present disclosure.

FIG. 5 shows an energy applicator 500 according to an embodiment of the present disclosure that is similar to the energy applicator 400 of FIG. 4, except for an electrically-conductive cylinder 540 disposed coaxially about a distal portion of the electrically-conductive layer 430. Electrically-conductive cylinder 540 may have a suitable length "L6" of a range from about 0.05 inches to about 0.2 inches. For example, the length "L6" may be selected to provide mechanical stability. In some embodiments, the distal edge of electrically-conductive cylinder 540 is disposed overlying the distal edge of the electrically-conductive layer 430. The shape and size of the electrically-conductive cylinder 540 may be varied from the configuration depicted in FIG. 5.

Figure 6:
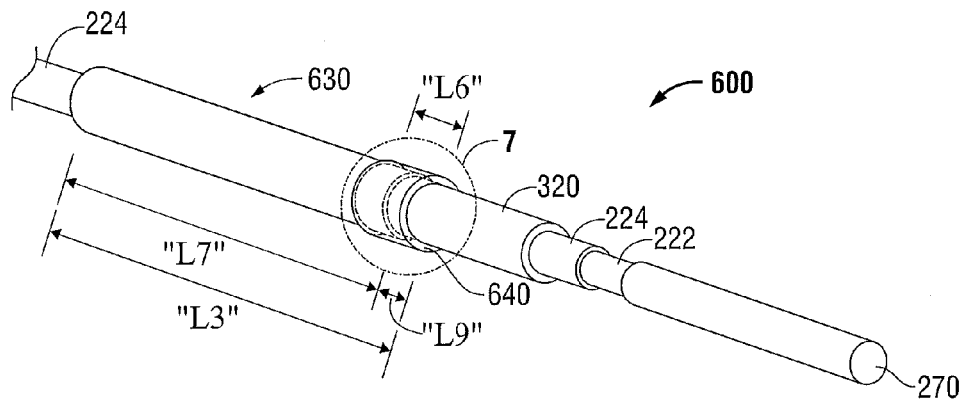
FIG. 6 is a perspective view of the portion of the energy applicator of FIG. 3 shown with another embodiment of an electrically-conductive layer and an electrically-conductive cylinder according to the present disclosure.

FIG. 6 shows an energy applicator 600 according to an embodiment of the present disclosure that includes an electrically-conductive layer 630 and an electrically-conductive cylinder 640. Electrically-conductive layer 630 surrounds a proximal portion of the dielectric layer 320 and is electrically coupled to the outer conductor 224, e.g., by solder or other suitable electrical connection. Electrically-conductive layer 630 is similar to the electrically-conductive layer 430 of FIG. 4, except that the electrically-conductive layer 630 has a length that is less than the length "L3" of the electrically-conductive layer 430. As shown in FIG. 6, the electrically-conductive layer 630 may have a length "L7", which is shorter than the length "L3" by a length "L9".

Figure 7:
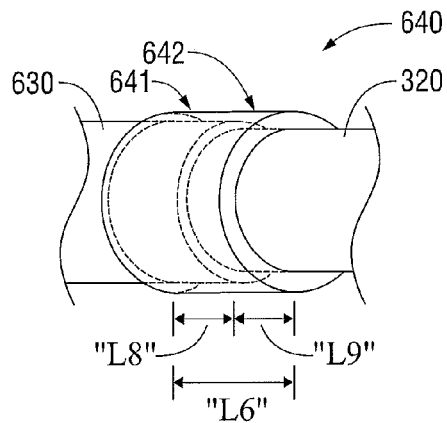
FIG. 7 is an enlarged view of the indicated area of detail of FIG. 6 according to an embodiment of the present disclosure.

Electrically-conductive cylinder 640 shown in FIGS. 6 and 7 is similar to the electrically-conductive cylinder 540 of FIG. 5, except that the electrically-conductive cylinder 640 extends distally beyond the distal edge of the electrically-conductive layer 630. As shown in FIG. 7, the electrically-conductive cylinder 640, having a length "L6", includes a first portion 641, having a length "L8", disposed coaxially about the distal end of the electrically-conductive layer 630, and a second portion 642, having a length "L9", disposed proximally to the first portion 641, surrounding a portion of the dielectric layer 320 distally extending beyond the electrically-conductive layer 630. In some embodiments, the electrically-conductive cylinder 640 is positioned relative to the distal edge of the electrically-conductive layer 630 such that the combined length of the electrically-conductive layer 630 and the electrically-conductive cylinder 640 is a length "L3", which may be, for example, a quarter wavelength or a half wavelength. The shape and size of the electrically-conductive cylinder 640 may be varied from the configuration depicted in FIGS. 6 and 7.

Figure 8:
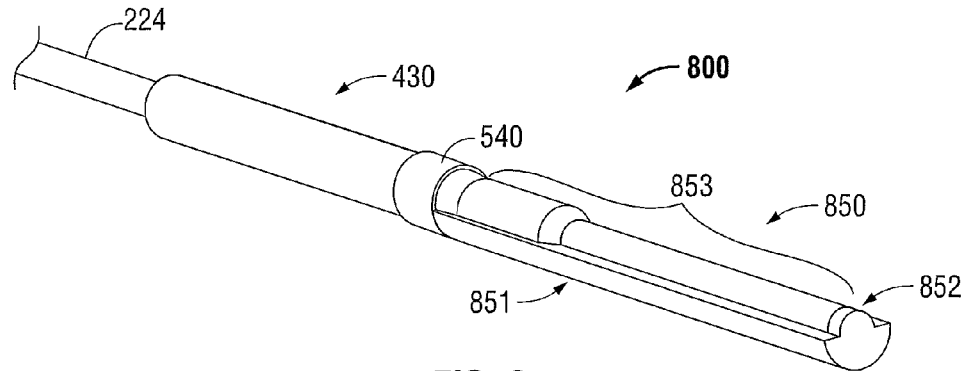
FIG. 8 is a perspective view of the portion of the energy applicator of FIG. 5 shown with a dielectric structure disposed distal to the electrically-conductive cylinder according to an embodiment of the present disclosure.

FIG. 8 shows an energy applicator 800 according to an embodiment of the present disclosure that is similar to the energy applicator 500 of FIG. 5, except for a generally longitudinally-disposed dielectric structure 850. In some embodiments, the dielectric structure 850 includes a dielectric cap configured to cover the distal end of the electrically-conductive member 270. As shown in FIG. 8, the dielectric structure 850 may be disposed distally to the electrically-conductive cylinder 540. Dielectric structure 850 may be formed using over-molding techniques or other forming techniques. In some embodiments, the dielectric structure 850 is formed from a material with a dielectric constant in the range of about 1.7 to about 10. The shape and size of the dielectric structure 850 may be varied from the configuration depicted in FIG. 8.

In some embodiments, the dielectric structure 850 includes a first dielectric segment 851, a second dielectric segment 852, and a third dielectric segment 853. As shown in FIG. 8, the first dielectric segment 851 extends distally from the distal end of the electrically-conductive cylinder 540 and may have a substantially half-cylindrical shape. First dielectric segment 851 may be made to encompass any radial angle. In some embodiments, the first dielectric segment 851 extends from the distal end of the electrically-conductive cylinder 540 to distal end of the electrically-conductive member 270. Second dielectric segment 852 is configured to cover the distal end of the electrically-conductive member 270. In some embodiments, the first and second dielectric segments 851, 852 are integrally formed in a molding process. First dielectric segment 851, the second dielectric segment 852 and the third dielectric segment 853 may each be formed by any suitable process.

Figure 9:
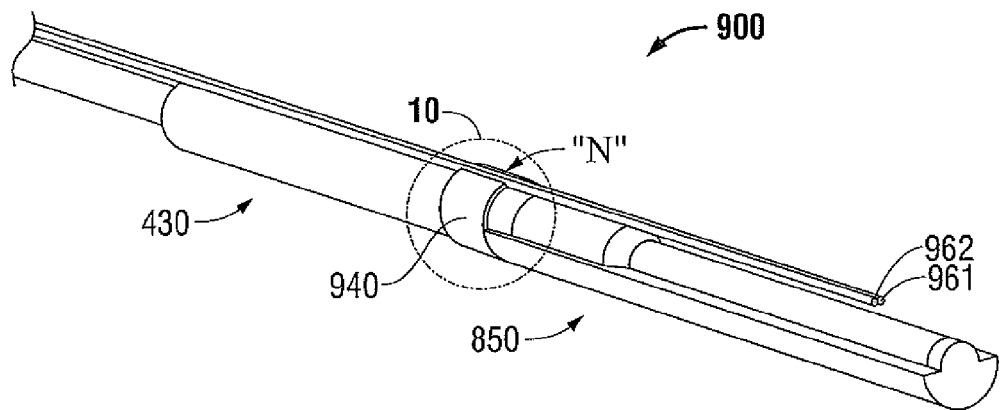
FIG. 9 is a perspective view of the portion of the energy applicator of FIG. 8 shown with a fluid inflow tube and a fluid outflow tube according to an embodiment of the present disclosure.

FIG. 9 shows an energy applicator 900 according to an embodiment of the present disclosure that is similar to the energy applicator 800 of FIG. 8, except for a longitudinally-extending inflow tube 961, a longitudinally-extending outflow tube 962, and an electrically-conductive cylinder 940 having a notch "N" defined therein that is configured to receive the inflow and outflow tubes 961, 962. In some embodiments, the inflow and outflow tubes 961, 962 are configured to supply and/or dispense coolant fluid (e.g., saline, water or other suitable coolant fluid) into and out of a distal portion of a cooling chamber (e.g., 1390 shown in FIG. 13). A pump (not shown) may be connected in fluid communication between the cooling chamber and a coolant source (e.g., 18 shown in FIG. 1). Inflow and outflow tubes 961, 962 may include thin-walled polyimide tubes. In some embodiments, a pump (not shown) supplies coolant fluid from a coolant source (e.g., 18 shown in FIG. 1) to one or more inflow tubes 961 which, in turn, deliver coolant fluid (e.g., "F" shown in FIG. 13B) to the cooling chamber (e.g., 1391 shown in FIG. 13B). Additionally, or alternatively, a pump may be fluidly coupled to one or more outflow tubes 962 to draw coolant fluid out of the cooling chamber.

Figure 10:
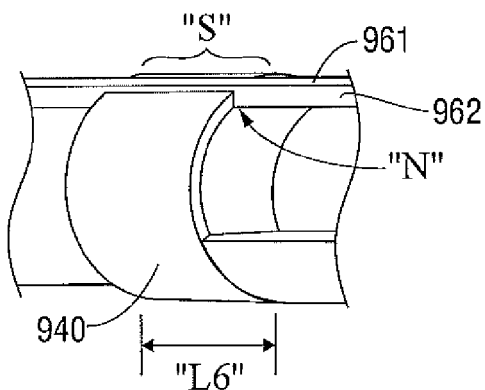
FIG. 10 is an enlarged view of the indicated area of detail of FIG. 9 according to an embodiment of the present disclosure.

As shown in FIGS. 9 and 10, the inflow and outflow tubes 961, 962 may extend longitudinally across the full length of the electrically-conductive layer 430 and at least partially across the dielectric structure 850. As shown in FIG. 10, a portion or segment "S" of the inflow and outflow tubes 961, 962 is disposed within a notch "N" defined within the electrically-conductive cylinder 940. In some embodiments, the notch "N" is configured as a recess, e.g., in the form of a groove or hole. In other embodiments, the notch "N" is configured as a first recess (not shown) and a second recess (not shown), wherein the first recess is configured to receive one or more inflow tubes 961 and the second recess is configured to receive one or more outflow tubes 962. Inflow tube 961 and the outflow tube 962 may be formed to have the same diameters or different diameters. Inflow and outflow tubes 961, 962 may have any suitable length. In some embodiments, the segment "S" of the inflow and outflow tubes 961, 962 is disposed between the electrically-conductive layer 430 and the outer circumferential surface of the electrically-conductive cylinder 940, which helps minimize the outer diameter of the device. Inflow and outflow tubes 961, 962 may be held in place, e.g., along the electrically-conductive layer 430 and/or within the notch "N", by using UV adhesive or other similar suitable adhesives, as well as heat shrink tubing or by other suitable methods. The shape and size of the inflow and outflow tubes 961, 962, the electrically-conductive cylinder 940 and the notch "N" may be varied from the configurations depicted in FIGS. 9 and 10.

Figure 11A:
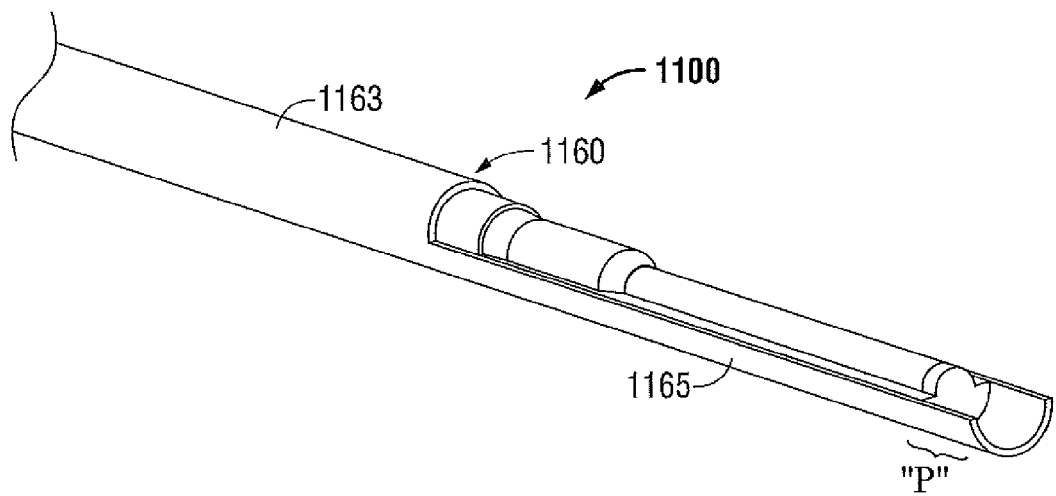
FIG. 11A is a perspective view of the portion of the energy applicator of FIG. 8 shown with a sleeve member surrounding a distal portion of the energy applicator according to an embodiment of the present disclosure.

FIG. 11A shows an energy applicator 1100 according to an embodiment of the present disclosure that is similar to the energy applicator 800 of FIG. 8, except for a sleeve member 1160. Sleeve member 1160 may be an elongated tubular body of a catheter assembly. As shown in FIG. 11A, the sleeve member 1160 may include a first sleeve portion 1163 and a second sleeve portion 1165 disposed distally to the first sleeve portion 1163. First sleeve portion 1163 may be configured to coaxially surround a proximal portion of the energy applicator 1100. Second sleeve portion 1165 may be configured to partially surround a distal portion of the energy applicator 1100. In some embodiments, the first sleeve portion 1163 has a substantially cylindrical shape, and the second sleeve portion 1165 has a substantially half-cylindrical shape. According to an embodiment of the present disclosure, an opening or electromagnetic "window" shown generally as "W" in FIGS. 12A through 14 is partially defined by the longitudinal edges of the second sleeve portion 1165. Second sleeve portion 1165 may include an engagement portion "P", which extends beyond the distal end of the dielectric structure 850.

Sleeve member 1160 may be formed of a suitable electrically conductive material such as metal or polymeric material. A suitable metal may include, for example, stainless steel, titanium, titanium alloys such as nickel-titanium and titanium-aluminum-vanadium alloys, aluminum, aluminum alloys, tungsten carbide alloys or combinations thereof. A suitable polymeric material may include, for example, thermoplastics including reinforced or unreinforced polymers, e.g., polyamide (nylon) or polyaramid (e.g., KEVLAR® manufactured by E.I. du Pont de Nemours and Company of Wilmington, Del., United States), or any suitable polymeric composite, e.g., polymers filled with carbon particles, silica, conductive particles such as metal particles or conductive polymers, or combinations thereof.

Figure 11B:
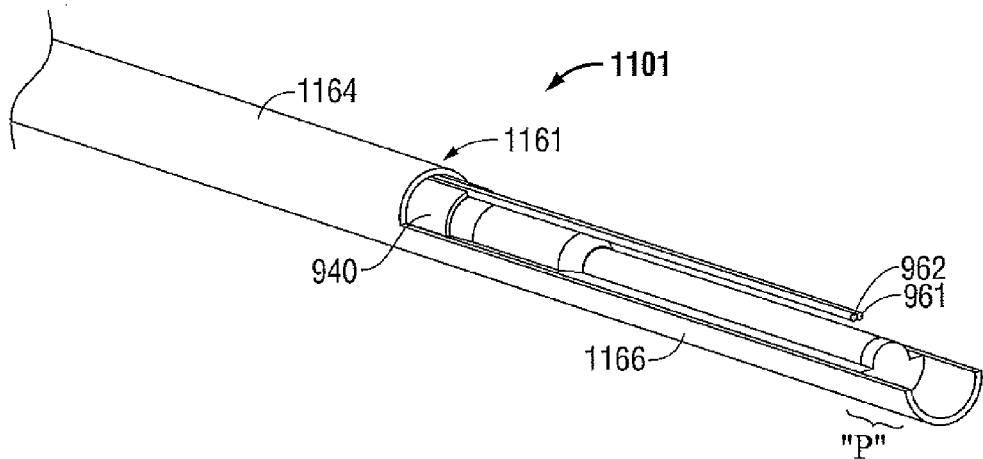
FIG. 11B is a perspective view of the portion of the energy applicator of FIG. 9 shown with a sleeve member surrounding a distal portion of the energy applicator according to an embodiment of the present disclosure.

FIG. 11B shows an energy applicator 1101 according to an embodiment of the present disclosure that is similar to the energy applicator 900 of FIG. 9, except for a sleeve member 1161. Energy applicator 1101 includes the inflow and outflow tubes 961, 962 shown in FIGS. 9 and 10. As shown in FIG. 11B, the sleeve member 1161 may include a first sleeve portion 1164 and a second sleeve portion 1166 disposed distally to the first sleeve portion 1164. Portions of the inflow and outflow tubes 961, 962 disposed proximal to the electrically-conductive cylinder 940 are covered by the first sleeve portion 1164. Sleeve member 1161 is similar to the sleeve member 1160 shown in FIG. 11A, and further description thereof is omitted in the interests of brevity.

Figure 12A:
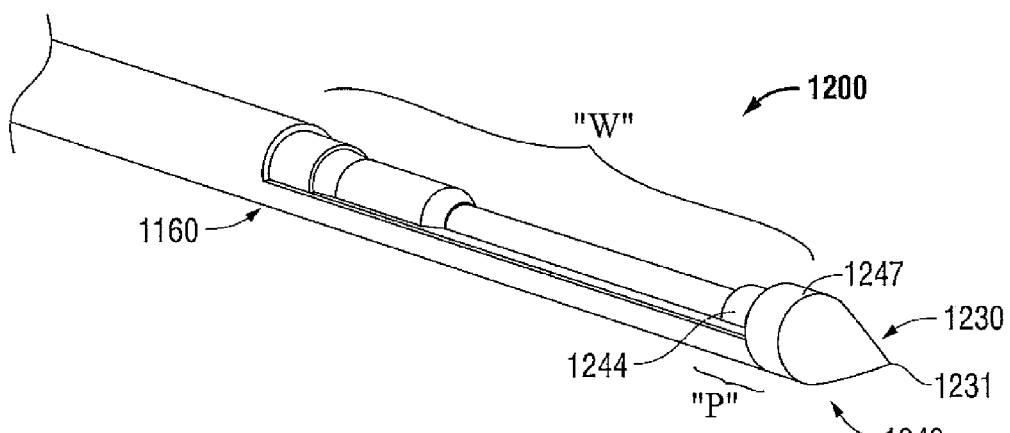
FIG. 12A is a perspective view of the portion of the energy applicator of FIG. 11A shown with an end member coupled to the distal end of the sleeve member according to an embodiment of the present disclosure.

FIG. 12A shows an energy applicator 1200 according to an embodiment of the present disclosure that is similar to the energy applicator 1100 of FIG. 11A, except for an end member 1240. End member 1240, or portions thereof, may be formed of a suitable non-conductive material, such as, for example, ULTEM®. End member 1240, or portions thereof, may be formed of a suitable conductive material such as metal, e.g., stainless steel. End member 1240 may include one or more conductive materials and/or one or more non-conductive materials. In some embodiments, the end member 1240 includes a shoulder portion 1244 having a generally cylindrical shape having a proximal end and a distal end. Shoulder portion 1244 may be configured to engage an engagement portion (e.g., "P" shown in FIGS. 11A and 12A) disposed at the distal end of the sleeve member 1160. The shape and size of the shoulder portion 1244 may be varied from the configuration depicted in FIG. 12A.

In some embodiments, the end member 1240 includes a central portion 1247 having a generally cylindrical shape having a proximal end and a distal end, wherein the proximal end of the central portion 1247 is coupled to the distal end of the shoulder portion 1244. Additionally, or alternatively, the end member 1240 may include a tapered portion 1230 extending distally from the distal end of the central portion 1247. Tapered portion 1230 may terminate in a sharp tip 1231 to allow for insertion into tissue with minimal resistance. In those cases where the energy applicator is inserted into a pre-existing opening, the tip 1231 may be rounded or flat. The shape and size of the central portion 1247 and tapered portion 1230 may be varied from the configuration depicted in FIG. 12A.

Figure 12B:
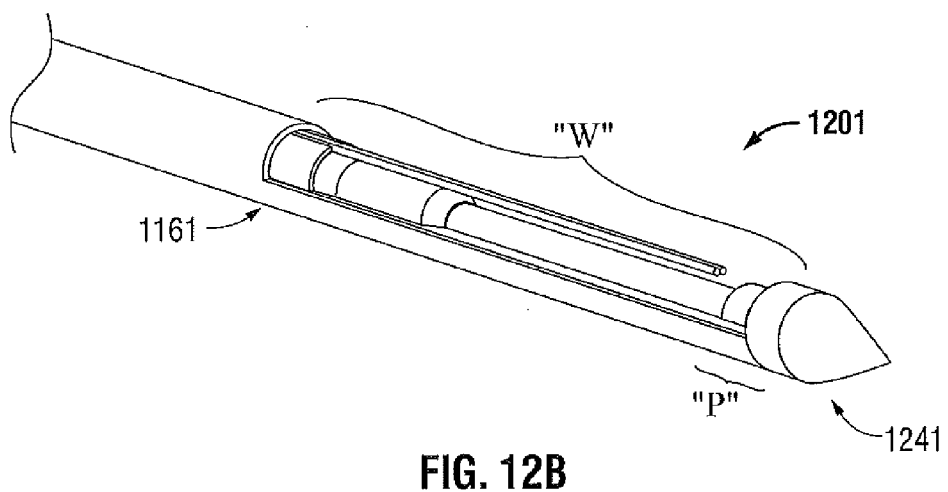
FIG. 12B is a perspective view of the portion of the energy applicator of FIG. 11B shown with an end member coupled to the distal end of the sleeve member according to an embodiment of the present disclosure.

FIG. 12B shows an energy applicator 1201 according to an embodiment of the present disclosure that is similar to the energy applicator 1101 of FIG. 11B, except for an end member 1241. End member 1241 is similar to the end member 1240 shown in FIG. 12A, and further description thereof is omitted in the interests of brevity.

Figure 13A:
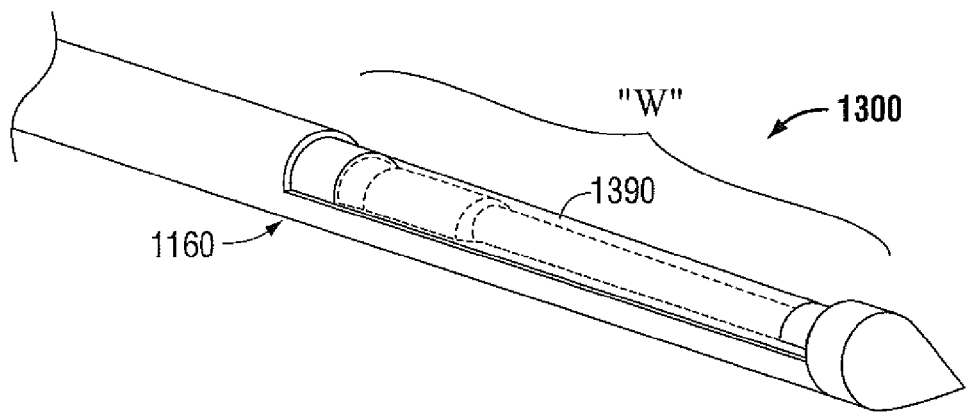
FIG. 13A is a perspective view of the portion of the energy applicator of FIG. 12A shown with a longitudinal chamber disposed between the electrically-conductive cylinder and the end member according to an embodiment of the present disclosure.

FIG. 13A shows an energy applicator 1300 according to an embodiment of the present disclosure that is similar to the energy applicator 1200 of FIG. 12A, except for a generally longitudinally-disposed dielectric member 1390. Dielectric member 1390 may be formed of an insulating material, such as, for example, a polyimide or similar dielectric material, to avoid shielding microwave radiation around the antenna assembly. Dielectric member 1390 may be formed over a portion of the dielectric structure 850 by a suitable molding process.

Figure 13B:
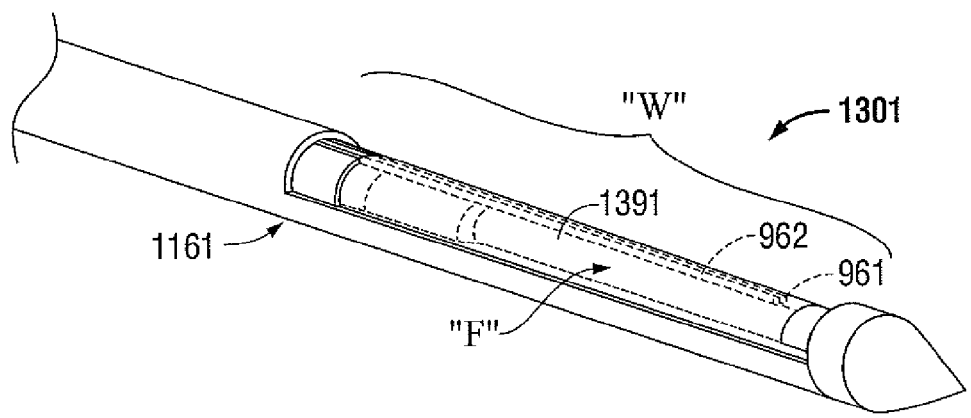
FIG. 13B is a perspective view of the portion of the energy applicator of FIG. 12B shown with a longitudinal chamber disposed between the electrically-conductive cylinder and the end member according to an embodiment of the present disclosure.

FIG. 13B shows an energy applicator 1301 according to an embodiment of the present disclosure that is similar to the energy applicator 1201 of FIG. 12B, except for a generally longitudinally-disposed chamber 1391 (also referred to herein as a cooling chamber). Energy applicator 1301 includes one or more inflow tubes 961 and one or more outflow tubes 962. Portions of the inflow and outflow tubes 961, 962 are disposed within the cooling chamber 1391, as shown in phantom lines in FIG. 13B. Inflow and outflow tubes 961, 962 are configured to supply and/or dispense coolant fluid "F" (e.g., saline, water or other suitable coolant fluid) into and out of a distal portion of the cooling chamber 1391. Cooling chamber 1391 may be disposed at least partially about an electrically-conductive member (e.g., 270 shown in FIG. 6). The shape and size of the inflow and outflow tubes 961, 962 and the cooling chamber 1391 may be varied from the configuration depicted in FIG. 13B.

Figure 14:
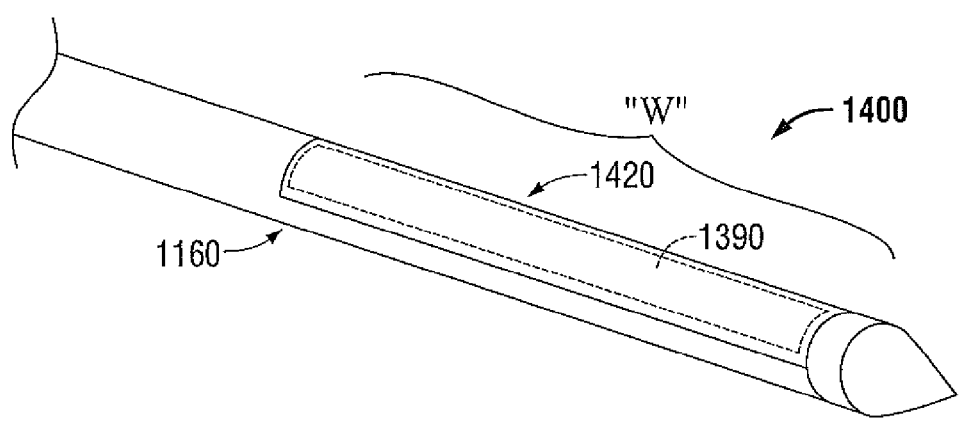
FIG. 14 is a perspective view of the portion of the energy applicator of FIG. 13A shown with a material layer disposed in an outer portion of the window according to an embodiment of the present disclosure.

FIG. 14 shows an energy applicator 1400 according to an embodiment of the present disclosure that is similar to the energy applicator 1300 of FIG. 13A, except for a material 1420 disposed over the dielectric member 1390. Material 1420 may be deposited in an over-molding process. Material 1420 may be a nonconductive radio frequency transparent material, e.g., a glass fiber epoxy composite or polyimide. In some embodiments, the dielectric materials filling the coaxial structure at the site of the opening "W" may vary in dielectric constant with shells or more complex dielectric layering to achieve the optimum antenna directivity and energy to tissue delivery.

Energy applicator 1400 may include an indicia alignment mark (not shown) such as a colored strip or the like, e.g., to provide a visual cue to the surgeon to allow orientation of the direction of flow of the energy to coincide with the indicia alignment mark. Additionally, or alternatively, the energy applicator 1400 may include indicia graduation marks (not shown) for insertion depth reference, e.g., to indicate the position of the opening (e.g., "W" shown in FIG. 17) relative to the surface of the tissue "T". Examples of indicia alignment mark and the indicia graduation mark embodiments are disclosed in commonly assigned U.S. patent application Ser. No. 12/476,960 filed on Jun. 2, 2009, entitled "ELECTROSURGICAL DEVICES WITH DIRECTIONAL RADIATION PATTERN".

The outer surface of the energy applicator 1400 may be coated with a suitable lubricious substance, such as TEFLON®, to aid in the movement of the energy applicator 1400 in or through tissue as well as to aid in preventing tissue from sticking to the outer surface of the device.

Figure 15:
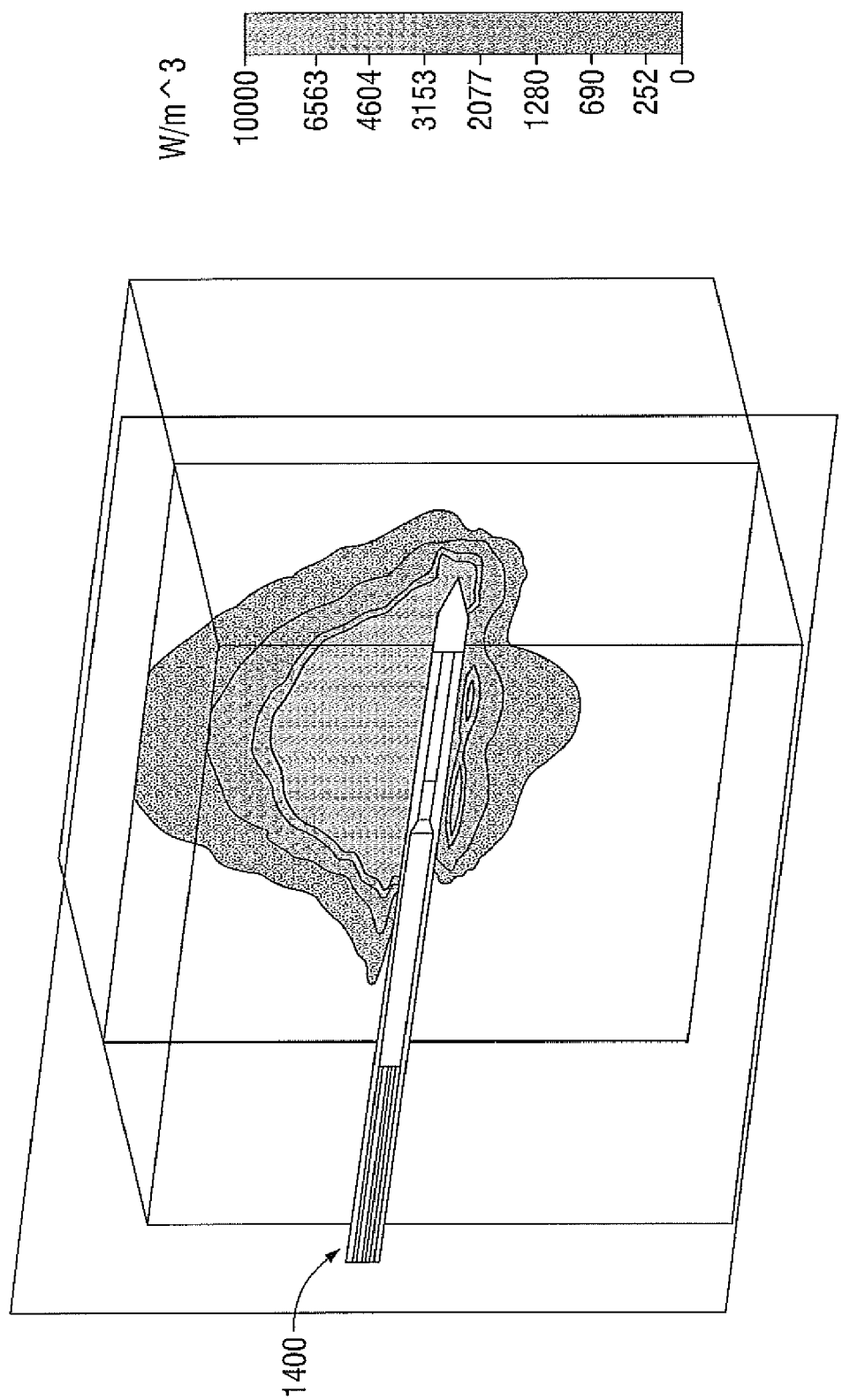
FIG. 15 is a cross-sectional view of an energy applicator shown with a diagrammatic representation of an emitted radiation pattern according to an embodiment of the present disclosure.
Figure 16:
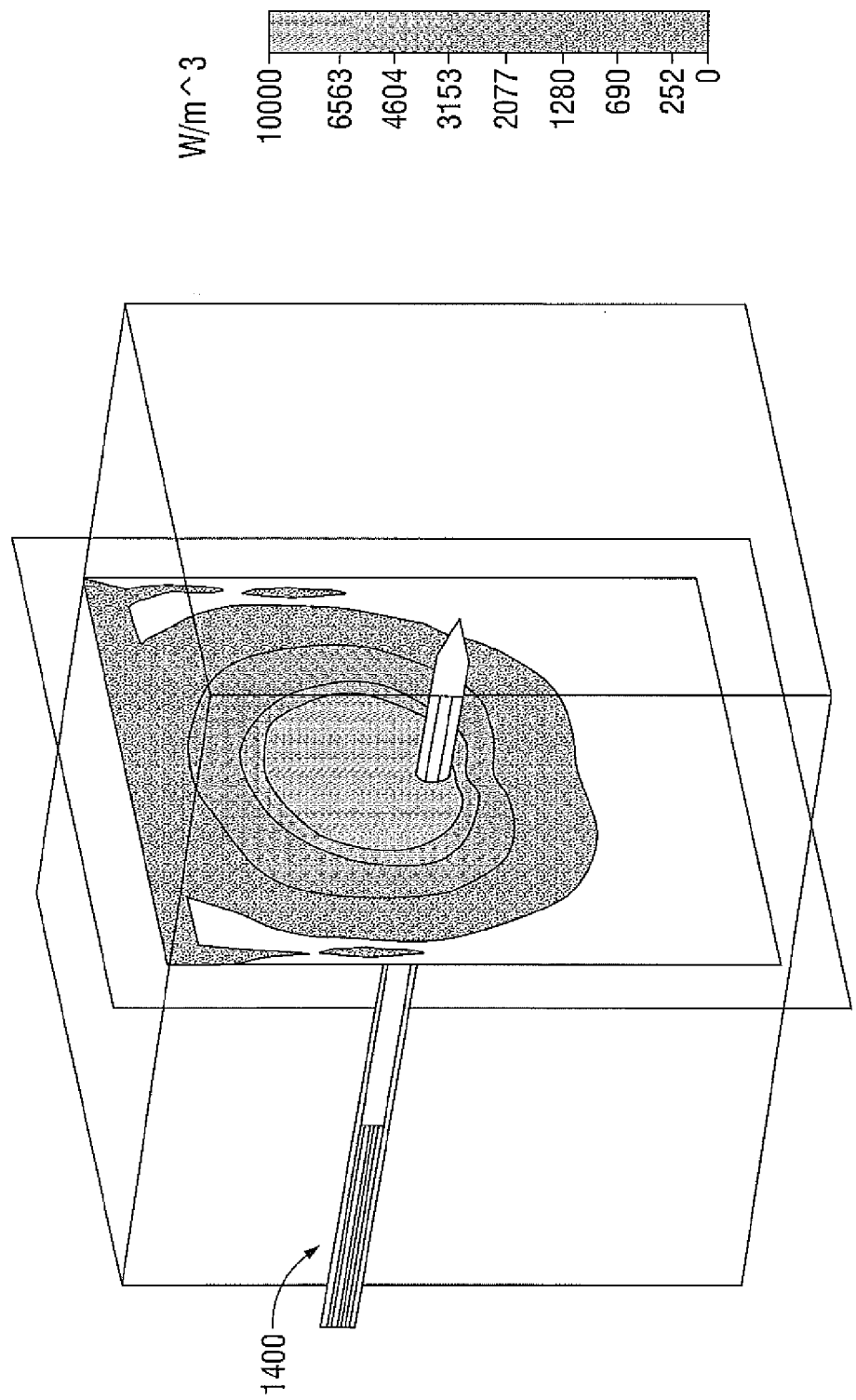
FIG. 16 is a cross-sectional view of another embodiment of an energy applicator shown with a diagrammatic representation of an emitted radiation pattern according to the present disclosure.

FIGS. 15 and 16 show a cross section of an energy applicator (e.g., 1400 shown in FIG. 14) according to an embodiment of the present disclosure that may be suitable for use in tissue ablation applications. FIGS. 15 and 16 show examples of directional radiation patterns emitted by the energy applicator 1400 according to embodiments of the present disclosure.

Figure 17:
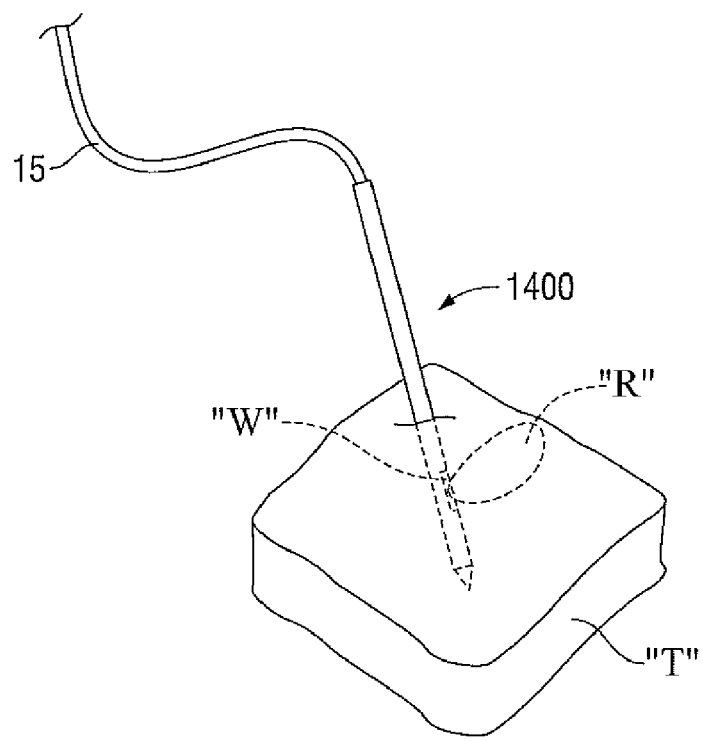
FIG. 17 is a diagrammatic representation of a radiation pattern of electromagnetic energy delivered into tissue by an energy applicator, such as the energy applicator of FIG. 14, according to an embodiment of the present disclosure.

FIG. 17 shows an embodiment of an energy applicator (e.g., 1400 shown in FIG. 14) coupled to a transmission line 15 according to the present disclosure. Transmission line 15 may connect the energy applicator 1400 to a power generating source, e.g., a microwave or RF electrosurgical generator. During a procedure, e.g. an ablation procedure, the energy applicator 1400 is inserted into or placed adjacent to tissue "T" and energy is supplied thereto. Energy applicator 1400 may be placed percutaneously or atop tissue. Ultrasound or computed tomography (CT) guidance may be used to accurately guide the energy applicator 1400 into the area of tissue "T" to be treated.

Energy applicator 1400 may be rotatable about a longitudinal axis "A-A" (shown in FIG. 2) such that the directional radiation pattern "R" rotates therewith. Examples of antenna assemblies rotatable about axis "A-A" such that any elongated radiation lobes rotates therewith are disclosed in commonly assigned U.S. patent application Ser. No. 12/197,405 filed on Aug. 25, 2008, entitled "MICROWAVE ANTENNA ASSEMBLY HAVING A DIELECTRIC BODY PORTION WITH RADIAL PARTITIONS OF DIELECTRIC MATERIAL".

Figure 18:
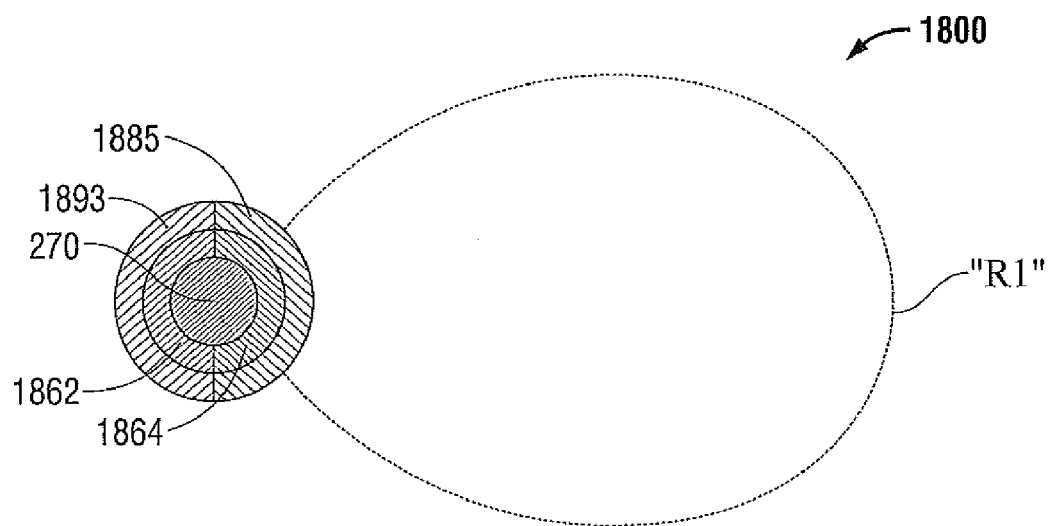
FIG. 18 is a cross-sectional view of an energy applicator shown with a diagrammatic representation of an emitted radiation pattern according to an embodiment of the present disclosure.
Figure 19:
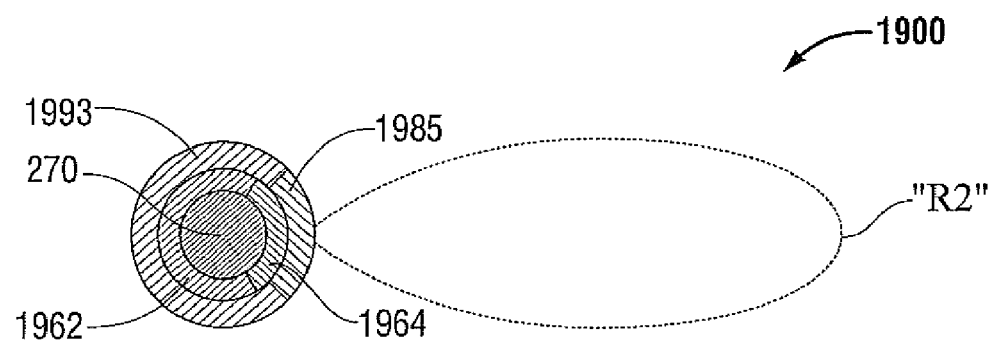
FIG. 19 is a cross-sectional view of another embodiment of an energy applicator shown with a diagrammatic representation of an emitted radiation pattern according to the present disclosure.
Figure 20:
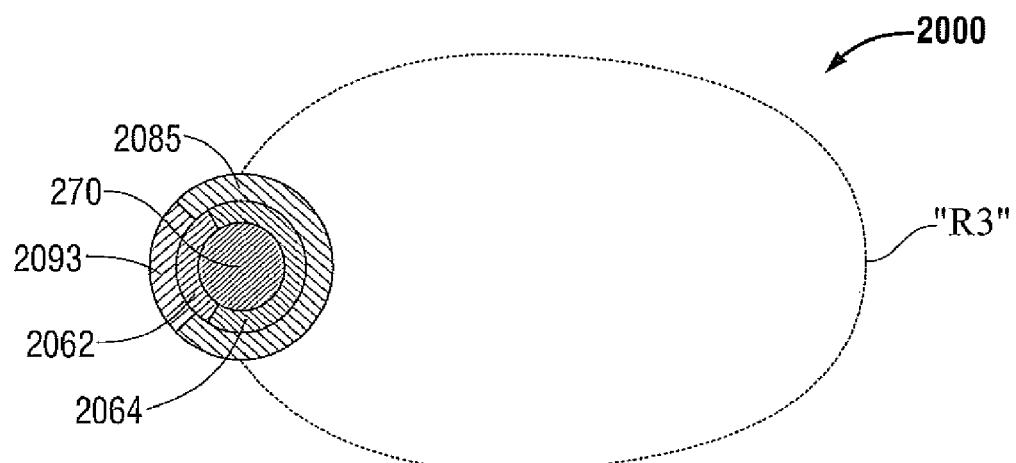
FIG. 20 is a cross-sectional view of yet another embodiment of an energy applicator shown with a diagrammatic representation of an emitted radiation pattern according to the present disclosure.

FIGS. 18 through 20 show various configurations of dielectric material at the site of an opening or electromagnetic "window" (e.g., "W" shown in FIG. 17) of an energy applicator (e.g., 1400 shown in FIG. 17) and examples of emitted directional radiation patterns, according to embodiments of the present disclosure.

FIG. 18 shows a cross-sectional view of an energy applicator 1800 and an emitted radiation pattern "R1" of microwave energy radiated therefrom. In FIG. 18, the window is approximately ½ the circumference of the sleeve member 1893 thereof. A first dielectric structure 1864 and a second dielectric structure 1862 are coupled to an inner conductor 270 at the site of the window. Inner conductor 270 may be similar to the inner conductor 220 shown in FIG. 2. First and second dielectric structures 1864, 1862 may have substantially the same diameter. Second dielectric structure 1862 may be similar to the first dielectric segment 851 shown in FIG. 8. In the embodiment depicted in FIG. 18, the sleeve member 1893 extends over the second dielectric structure 1862. The window in the sleeve member is filled with a radio frequency (RF) transparent material 1885, e.g., a glass fiber epoxy composite or polyimide.

FIG. 19 shows a cross-sectional view of an energy applicator 1900 and an emitted radiation pattern "R2" of microwave energy radiated therefrom. In the energy applicator 1900, the window is approximately ¼ the circumference of the sleeve member 1993 thereof. A first dielectric structure 1964 and a second dielectric structure 1962 are coupled to the inner conductor 270 at the site of the window. In the embodiment depicted in FIG. 19, the sleeve member 1993 extends fully over the second dielectric structure 1962 and partially over the first dielectric structure 1964. The window in the sleeve member 1993 of the energy applicator 1900 is filled with a RF transparent material 1985.

FIG. 20 shows a cross-sectional view of an energy applicator 2000 and an emitted radiation pattern "R3" of microwave energy radiated therefrom. In the energy applicator 2000, the window is approximately ⅘ the circumference of the sleeve member 2093. A first dielectric structure 2064 and a second dielectric structure 2062 are coupled to the inner conductor 270 at the site of the window. In the embodiment depicted in FIG. 20, the window and the RF transparent material 2085 disposed therein extends fully over the first dielectric structure 2064 and partially over the second dielectric structure 2062.

Hereinafter, a method of manufacturing an energy applicator or probe having a dielectric loaded coaxial aperture with distally positioned resonant structure, in accordance with the present disclosure, is described with reference to FIG. 21. It is to be understood that the steps of the method provided herein may be performed in combination and in a different order than presented herein without departing from the scope of the disclosure.

Figure 21:
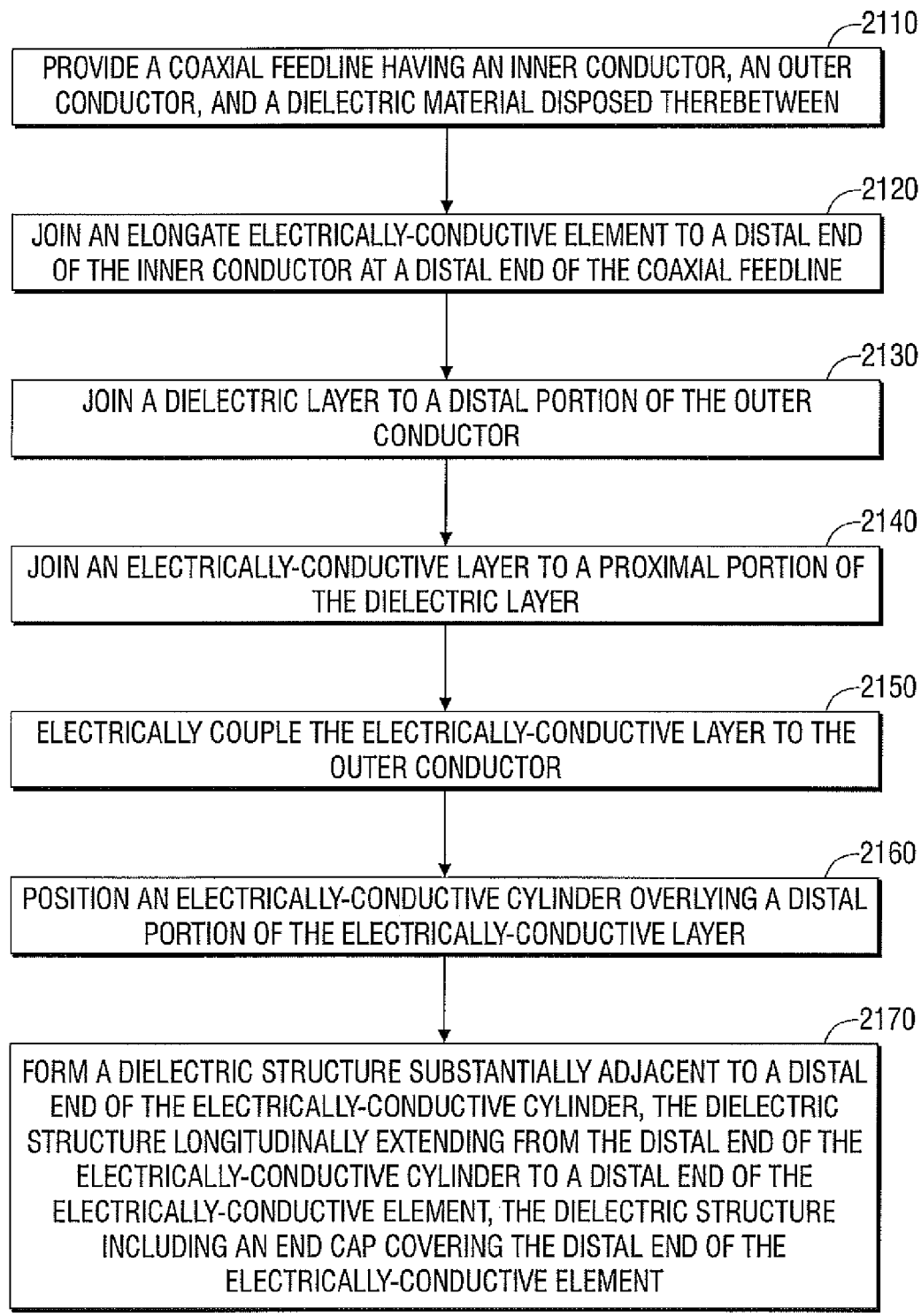
FIG. 21 is a flowchart illustrating a method of manufacturing an electrosurgical device according to an embodiment of the present disclosure.

FIG. 21 is a flowchart illustrating a method of manufacturing an electrosurgical device according to an embodiment of the present disclosure. In step 2110, a coaxial feedline (e.g., 226 shown in FIG. 2) is provided. The coaxial feedline includes an inner conductor (e.g., 220 shown in FIG. 2), an outer conductor (e.g., 224 shown in FIG. 2), and a dielectric material (e.g., 222 shown in FIG. 2) disposed therebetween. A portion of the inner conductor and the dielectric material (e.g., 221 shown in FIG. 2) may extend beyond the outer conductor at the distal end of the coaxial feedline.

In step 2120, an elongated electrically-conductive member (e.g., 270 shown in FIG. 2) is joined to the distal end of the inner conductor (e.g., 220 shown in FIG. 2) at a distal end of the coaxial feedline. In some embodiments, the electrically-conductive member is a solid metal cylinder electrically coupled to the inner conductor, e.g., by solder or other suitable electrical connection.

In step 2130, a dielectric layer (e.g., 320 shown in FIG. 3) is joined to a distal portion of the outer conductor (e.g., 224 shown in FIG. 3). In some embodiments, the dielectric layer is spaced apart from and disposed proximal to the distal end of the outer conductor.

In step 2140, an electrically-conductive layer (e.g., 430 shown in FIG. 4) is joined to a proximal portion of the dielectric layer (e.g., 320 shown in FIG. 4). In some embodiments, a portion of the dielectric layer extends distally beyond the electrically-conductive layer, e.g., to direct current into a coaxial choke network or balun structure.

In step 2150, the electrically-conductive layer is coupled to the outer conductor of the coaxial feedline. In some embodiments, the electrically-conductive layer includes a first portion (e.g., 431 shown in FIG. 4) disposed coaxially about a proximal portion of the dielectric layer, and a second portion (e.g., 432 shown in FIG. 4) disposed proximally to the first portion, the second portion electrically coupled to the outer conductor.

In step 2160, an electrically-conductive cylinder (e.g., 540 shown in FIG. 5) is positioned overlying a distal portion of the electrically-conductive layer (e.g., 430 shown in FIG. 5). In some embodiments, a portion (e.g., 642 shown in FIG. 7) of the electrically-conductive cylinder (e.g., 640 shown in FIGS. 6 and 7) extends distally beyond the distal edge of the electrically-conductive layer (e.g., 630 shown in FIG. 7). In some embodiments, the electrically-conductive cylinder is positioned relative to the distal edge of the electrically-conductive layer such that the combined length of the electrically-conductive layer and the electrically-conductive cylinder is a quarter wavelength or a half wavelength.

In step 2170, a dielectric structure (e.g., 850 shown in FIG. 8) is formed having a proximal end disposed substantially adjacent to a distal end of the electrically-conductive cylinder, wherein the dielectric structure longitudinally extends from the distal end of the electrically-conductive cylinder to a distal end of the electrically-conductive member. In some embodiments, the dielectric structure includes a dielectric cap (e.g., 852 shown in FIG. 8) configured to cover the distal end of the electrically-conductive member. The dielectric structure may be formed using over-molding techniques or other forming techniques.

The above-described electrosurgical devices for treating tissue and methods of directing electromagnetic radiation to a target volume of tissue may be used to provide directional microwave ablation, wherein the heating zone may be focused to one side of the electrosurgical device, thereby allowing clinicians to target small and/or hard to access tumors without having to penetrate the tumor directly or kill more healthy tissue than necessary. The presently disclosed electrosurgical devices may allow clinicians to avoid ablating critical structures, such as large vessels, healthy organs or vital membrane barriers, by placing the electrosurgical device between the tumor and critical structure and directing the electromagnetic radiation toward the tumor and away from the critical structure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical device for directing energy to a target volume of tissue, comprising:
    a coaxial feedline having an inner conductor, an outer conductor coaxially disposed around the inner conductor, and a dielectric material disposed therebetween;
    an elongated electrically-conductive member longitudinally disposed at a distal end of the inner conductor;
    a balun including:
        a dielectric layer coaxially disposed around a distal portion of the outer conductor of the feedline; and
        an electrically-conductive layer coaxially disposed around a proximal portion of the dielectric layer, wherein the dielectric layer extends distally beyond a distal end of the electrically-conductive layer;

an electrically-conductive cylinder coaxially disposed around a distal portion of the balun; and a dielectric structure disposed substantially adjacent to a distal end of the electrically-conductive cylinder, wherein the dielectric structure longitudinally extends from the distal end of the electrically-conductive cylinder to a distal end of the electrically-conductive member.

2. The electrosurgical device of claim 1, wherein a portion of the inner conductor and the dielectric material of the coaxial feedline extends beyond the outer conductor at a distal end of the coaxial feedline.

3. The electrosurgical device of claim 1, wherein the electrically-conductive member is electrically coupled to the inner conductor.

4. The electrosurgical device of claim 1, wherein the balun is a quarter-wave sleeve.

5. The electrosurgical device of claim 1, wherein the electrically-conductive layer includes a first portion coaxially disposed around the proximal portion of the dielectric layer, and a second portion disposed proximally to the first portion, the second portion electrically coupled to the outer conductor.

6. The electrosurgical device of claim 1, wherein the dielectric structure is configured to cover a distal end of the electrically-conductive member.

7. The electrosurgical device of claim 1, further comprising:

a cooling chamber disposed at least partially about the electrically-conductive member.

8. The electrosurgical device of claim 7, further comprising:

an inflow tube configured to supply a coolant fluid into the cooling chamber; and an outflow tube configured to dispense the coolant fluid from the cooling chamber.

9. The electrosurgical device of claim 8, further comprising:

a coolant source to supply the coolant fluid.

10. The electrosurgical device of claim 1, further comprising:

a sleeve member including a first sleeve portion and a second sleeve portion, the second sleeve portion disposed distally to the first sleeve portion, wherein the first sleeve portion is disposed proximal to the dielectric structure and the second sleeve portion is configured to partially surround the dielectric structure.

11. The electrosurgical device of claim 10, further comprising an electromagnetic window configured to emit a directional radiation pattern in operation.

12. The electrosurgical device of claim 11, wherein the electromagnetic window is partially defined by longitudinal edges of the second sleeve portion.

13. The electrosurgical device of claim 11, wherein the electromagnetic window includes a radio frequency (RF) transparent material.

14. The electrosurgical device of claim 10, wherein the second sleeve portion includes an engagement portion extending beyond a distal end of the dielectric structure.

15. The electrosurgical device of claim 1, further comprising a tapered portion having a tip configured to penetrate tissue.

* * * * *